United States Patent [19]

Pinckard

[11] 4,164,405
[45] Aug. 14, 1979

[54] METHOD OF CONTROLLING THE RATE OF DAMPING-OFF OF PLANT SEEDLINGS AND IMPROVING THE RATE OF TREE GROWTH WITH TREATED COTTON GIN WASTE

[75] Inventor: Joseph A. Pinckard, Inglis, Fla.

[73] Assignee: The Ekol Corporation, Ocala, Fla.

[21] Appl. No.: 887,963

[22] Filed: Mar. 20, 1978

Related U.S. Application Data

[63] Continuation-in-part of Ser. No. 544,669, Jan. 27, 1975, abandoned.

[51] Int. Cl.$^2$ ............................................. A01N 9/08
[52] U.S. Cl. ............................................. 71/79; 71/1; 71/3; 71/24; 424/115; 424/195
[58] Field of Search ...................... 424/115, 195; 71/1, 71/3, 79; 195/95

[56] References Cited
PUBLICATIONS

Alberson et al., "Composting Cotton Gin Waste", USDA-ARS, 42-102 (1974), pp. 1-16.
Willis, Wm., "Composting Cotton Gin Trash", La. Ag. Exp. Sta. Bull., No. 490 (1954), pp. 3-7.
Boodley et al., Plant Sciences Info. Bulletin #43 (Jul. 1972), pp. 1-8, New York State College of Ag. & Life Sciences.

Primary Examiner—V. D. Turner
Attorney, Agent, or Firm—Cushman, Darby & Cushman

[57] ABSTRACT

A biochemical process for the aerobic thermophyllic fermentation of cotton gin waste is disclosed which converts a presently useless pest ridden agricultural waste product into a useful medium for the culture of horticultural and agronomic plants as well as micoorganisms useful to man. By the aeration, water content and physical shape and size of the waste product, piles are so conditioned that by means of the resulting biodegradation processes plant pathogenic microorganisms, insects, viruses, spider mites and related pests are destroyed. Additionally, pesticidal residues, chemical plant growth regulators and certain harvest aid materials normally added to the growing cotton crop for production purposes are reduced to materials harmless to plant life. The resulting humus like material provides improved plant growth, nearly five times that of a good river loam soil, and contains a microbial population that prevents the spread of soil borne plant pathogenic microorganisms reintroduced into the medium. The aerobic thermophyllically fermented gin waste provides a medium for growing horticultural and other plants without sterilization with heat or the use of fungicides. It also provides a medium with a source of energy for the culture of microorganisms useful to man. The fermented gin waste may also be employed as a means for controlling the rate of damping-off of plant seedlings caused by plant parasitic fungi. Also, by placing the fermented gin waste about the locus of the roots of trees, growth may be promoted and decline controlled. The medium may further contain iron salts to provide added nutritional value.

15 Claims, 2 Drawing Figures

POSITION OF
THERMOMETER
A—OUTER 10"-12"
B—24"-30"
C—CENTER

METHOD OF CONTROLLING THE RATE OF DAMPING-OFF OF PLANT SEEDLINGS AND IMPROVING THE RATE OF TREE GROWTH WITH TREATED COTTON GIN WASTE

BACKGROUND OF THE INVENTION

This application is a continuation-in-part of Ser. No. 544,669, filed Jan. 27, 1975, and now abandoned.

This invention relates to the conversion of cotton gin waste to a humus-like substance having the properties of improving plant growth while at the same time suppressing or eliminating soil borne plant pathogenic microorganisms, viruses, insects, spider mites, weed seeds and certain organic insecticidal residues, herbicidal residues, chemical plant growth regulators and related agents harmful to plant and animal growth. Historically, suppression or elimination of soil borne pests of plants has been accomplished by means of applying heat to the mass of soil to be cleansed, the application of toxic gases as by fumigation and by the application of toxic chemicals as drenches or powders to the soil or plant growing medium. Many common horticultural plant growing media are formulations of sand, peat moss of various kinds, minerals such as vermiculite and perlite, plant foods, and agents to assist in wetting the mass. All such materials must by law be rendered free of pests by means of approved heat or chemical fumigation or treatment in order to be shipped or sold commercially.

The present art of formulating horticultural plant growing media precludes the use of certain agricultural organic residues because they contain many of the pests plant growers seek to avoid. Additionally, growers have found that if the media are not completely free of plant disease causing agents at the time of planting, a small contamination may spread wildly through the medium and the planting may be lost. For this reason agricultural waste products are commonly destroyed or abandoned in dumps or by other means and their value is lost.

A specific example is that of cotton gin waste. In the humid and irrigated areas of the cotton belt each 500-pound bale of cotton lint generates approximately 150 pounds of waste. A 10,000-bale gin in the Mississippi Delta produces about 800 tons of waste. In previous years this waste was burned in an open refuse burner. The smoke from the burners, unfortunately, contains toxic substances including the combustion products of the pesticidal chemicals and harvest aids, some of which may contain severe poisons such as arsenic. Beginning in 1974 the Environmental Protection Agency prohibited open burning of cotton gin waste. Because the material contains plant pests it cannot legally be moved off the premises of the gin unless certified free of pests by the U.S. Department of Agriculture, Animal and Plant Health Inspection Service. The net result is a large pile of gin waste which is almost impossible to handle after it begins to decay and becomes semi-liquid.

In areas where the crop is harvested with spindle pickers the cotton gin waste normally consists of the following materials:

PHYSICAL CONSTITUENTS

Seed (broken, immature, diseased) (wt.):10.0%
Motes (tangled knots of lint):8.0%
Leaves, stems, etc.:70.0%
Moisture:10-15.0%

CHEMICAL CONSTITUENTS

Protein (total nitrogen about 2.3%):15.00%
Fiber:20.00%
Phosphorus:00.38%
Potassium:00.10%
Iron:Traces
Pesticidal residues (roughly):250 ppm These constituents vary, for the most part, with the seasonal dates of harvest, the degree of disease, insect and weed infestations of the fields, weather and general vigor of the crop. However, several independent analyses of the waste or tailings indicate a stable chemical composition which is regulated by the genetics of the cotton plant. A normal clean crop will have a consistently stable composition similar to that given above.

At the present time all horticultural plant growing media, such as potting soil for growing plants, is sterilized by heat or chemical treatment or is formulated from pest free or sterile components, peat, expanded minerals and the like. One of the better examples of this is shown in Cornell University Information Bulletin 43, July 1972 at Pages 1–8.

If a pest bearing seed is planted in this type of media, or if contamination is accidentally introduced into the pest free or sterile media, the introduced pest has no competition and will run wild through the media destroying as it goes.

The utilization of cotton gin waste, or tailings, has been explored by many farmers, ginners and professional people since the invention of the gin. Its value as animal feed is well known except that today it normally contains pesticidal residues which prohibit its use for animal feed.

It is known to be an excellent organic fertilizer except that it contains plant disease causing agents, insects, weed seeds and pesticidal residues detrimental to plant growth. For this reason its movement is restricted by federal and state plant health regulations.

A method of composting gin waste was proposed by Willis in 1954 (Willis, W. H. Composting Cotton Gin Trash, La. Agri. Exp. Sta. Bul. No. 490, 1954) and by Alberson and Hurst, 1964. (Alberson, D. M. and W. M. Hurst, Composting Cotton Gin Waste. 1964. USDA, ARS 42-102, (16 pages, illus.)). Both investigators used the natural process or variations thereof which consisted of stacking the material in a pile, applying water and allowing fermentation to proceed.

My research has shown that to attempt to compost cotton gin waste as described by Willis, and by Alberson and Hurst, resulted in an anaerobic fermentation near the center of the pile which prevented the fermentation from going to completion while the outer several inches of the pile decayed very slowly, providing a cover for flies, other insects and rodents.

Alberson and Hurst and others (Staffeldt, E. E. 1959. Elimination of Verticillium albo-atrum by Composting Cotton Gin Waste, Plant Disease Reporter 43:1150–1152), have shown that composted cotton gin waste destroys the fungus causing verticillium wilt of cotton. However, again it must be emphasized that the natural method of composting as used by Alberson and Hurst, Willis and others, does not include the outer few inches of the compost pile which escapes the heating process. The natural method of composting does not cleanse the mass completely, nor does it comply with Federal requirements.

After repeating the composting processes of Willis and Alberson-Hurst and testing the end products produced by gin wastes from Louisiana, Arkansas and Mississippi, it was concluded that their processes were not sufficiently well controlled to meet the federal regulations of the Animal and Plant Health Inspection Service (APHIS) of the United States Department of Agriculture (USDA). In general, the federal regulations require that noxious weed seeds (of which there are several), dangerous insects (such as the pink boll worm), certain cotton plant diseases which are common to many plants and plant parasitic nematodes (such as root knot and soybean cyst) must not be present in the finished product if it is to be moved from the gin yard site. The original objective of both Willis and Alberson-Hurst was to so compost gin waste that it could be moved back on to the fields and pastures as a soil conditioning mulch and as a fertilizer.

The object of this invention is to provide a process for the conversion of raw gin waste into a type of humus that will not only meet the requirements of the Animal and Plant Health Inspection Service but also be of commercial value to the Horticultural and Biological professions.

A further object of the present invention is to provide a means for promoting growth of trees and shrubs.

Still yet a further object of the present invention is to provide a useful medium having a variety of horticultural uses.

These and other objects of the present invention will be more apparent from the discussion which follows.

SUMMARY OF THE INVENTION

The process of the present invention provides for the biological conversion (i.e. the aerobic, thermophyllic fermentation) of cotton gin waste, which converts a presently useless pest ridden agricultural waste material into a useful horticultural plant growing medium and source of energy for certain microorganisms.

Treatment of the cotton gin waste initially requires the building of large free standing windrows (i.e. piles) of cotton gin waste. The windrows need not be enclosed in bins or tanks. The windrows must be uniformly moistened with water, which preferably contains added iron salts.

Thermometers are inserted into the windrows at certain levels to monitor the temperature therein for control of the process and avoid burning of the pile. The temperature will begin to rise within 12 to 16 hours. Care should be exercised to avoid temperatures in excess of 180° F. Thus, should the temperature of the interior of the windrow rise quickly, the windrow must be rebuilt to prevent heat damage. While the temperature of the process can go as high as 180° F., it usually does not go above 160° F. and normally is between 130° and 150° F. The temperature of the freshly built pile of waste rises to a peak in about 24 to 48 hours after turning, with water added, and falls during the turning process several days later to ambient temperature (usually below 90° F., e.g. 32 to 85° F.). By means of adjusting the aeration, water content and physical shape and size of the waste product piles this waste material is so conditioned that by means of the resulting biodegradation processes plant pathogenic microorganisms, insects, viruses, spider mites and related pests are destroyed.

The water content is critical and must be maintained at about 1 to 5 times the dry weight of the original material; however, 2.5 to 3 times is a most preferred ratio. The normal dry weight is about 8 pounds per cubic foot. Optimum fermentation and temperature increase takes place at a total weight (i.e. wet weight) of 20 to 25 pounds per cubic foot.

Care should be taken in preparing the pile and systematically the outside of the pile is placed on the inside and additional water is added to maintain the required ratio, preferably 250–300% of the original dry weight. As the temperature rises and falls to about 130° F., the pile is turned again in the described pattern. Several turnings may be necessary to reduce sticks and bracts ("burrs") to a black friable humus.

The resulting humus material provides a horticultural medium for improved plant growth, nearly five times that of a good river loam soil. Unexpectedly, the material was found to contain anti-biotic agents capable of preventing the spread of soil borne plant pathogenic microorganisms introduced into the medium artificially. All of the organisms present in the cotton gin waste are not known, but those commonly present are mesophylic forms of bacteria, fungi and actinomycetes commonly found in soil at temperatures up to about 105° F. As the temperature increases, the ordinary fungi are normally killed and the thermophyllic fungi, bacteria and actinomycetes take over and increase the temperature up to 140° to 150° F. under optimum conditions. The large piles of waste, e.g. windows at least 10 feet wide and at least 8 feet high but preferably 30 feet high and 75 feet wide provide insulation useful in completing the process.

There are many known species of microorganisms producing about 100 known antibiotics of which about 10 to 15 are useful to man. In the present invention a large number of antibiotics and microbial biodegradation products are released in the cotton gin waste compost by a multiplicity of microbial species during the course of the fermentation, each rising to dominance, then fading into obscurity. Some of these antibiotic and microbial biodegradation compounds found in the processed gin waste as described herein are antagonistic to *Rhizoctonia solani* and other plant disease causing agents. Contrary to the usual situation in the ordinary soil there is a continuous regeneration of these antibiotics in the gin waste for several months through the energy conversion of the carbon and nitrogen present.

The biodegraded cotton gin waste of the invention is particularly valuable because of its ability to combat *Rhizoctonia solani* since at the present time there is no known commercial horticultural plant growing medium available that will block the spread of the plant pathogenic fungus *Rhizoctonia solani* it has been introduced into the medium.

The aerobic thermophilically fermented cotton gin waste disclosed herein provides a medium for growing horticultural and other plants without the use of chemical pesticides or heat of sterilization being applied. In this respect the true biological control of certain soil borne plant pathogenic microorganisms has been achieved. Thus, the fermented cotton gin waste produced in accordance with the present invention is useful as a vehicle for the cultivation of microorganisms beneficial to agriculture.

Unexpectedly, it has also been found that the aerobic thermophilically fermented cotton gin waste disclosed herein has an ameliorating effect on Young Tree Decline, particularly Young Tree Decline of citrus and peach trees. Furthermore, when placed about the locus of the roots of a tree, the fermented gin waste of the present invention has been found to improve the growth rate of the tree.

The fermented cotton gin waste appears to be unique in its properties. Thus, sugar cane bagasse does not behave in the same way as cotton gin waste.

Composted gin waste made by the present process exhibits the following properties:

1. Plant disease causing agents are destroyed.
2. Weed seeds of all kinds are destroyed.
3. Neither insects nor nematodes survive the process.
4. There will be no odor of ammonia or of putrifactive processes.
5. Organic type insecticidal poisons such as Toxaphene-DDT, Dieldrin or Aldrin originally applied to the growing cotton crop are removed.
6. Arsenic compounds applied as herbicides to the growing crop are tied up by the humus.
7. The use of gin waste compost, or humus, made by the present process, if mixed with clay soils at effective rates (e.g. as low as 10 to 15% gin waste humus and 85 to 90% red clay) will support double the plant growth produced on red clay alone. A 25% gin waste humus made by the present process mixed with 75% red clay will result in three times the growth of cotton seedlings (wet weight) normal for red clay.
8. Humus made from gin waste by the process if mixed with conventional horticultural growing media at rates of 25%, or more, will suppress the growth of soil borne plant parasitic fungi such as the Damping-Off fungus *Rhizoctonia solani* and *Phytophthora cinnamomi* the cause of Camellia Die-Back (Reference Miller, Univ. Fla., Gainesville 1978).
9. Humus made from cotton gin waste by the present process, if applied to the soil under the canopy of citrus trees and cut in with a disc at effective rates (e.g. 75 to 200 pounds and preferably 100 pounds per tree or 7,500 to 20,000 pounds and preferably 10,000 pounds per acre) will suppress the fruit tree decline disease of citrus known as Young Tree Decline and will also improve tree growth.
10. Mycorrhizal fungi added to the humus made from gin waste according to this process will survive and grow in this medium, as for example the mycorrhizal fungus Endogone.
11. Species of Rhizobia used for the inoculation of legume seed will survive and grow in the humus made from gin waste by the process, for example Rhizobium of soybean.

DETAILED DESCRIPTION OF THE INVENTION

According to the present invention, raw gin waste, as it is expelled from the gin, may either be blown into a pile or into wagons and hauled to a dump. The waste is compressed into bales ranging in size from 60 pounds to as much as 750 pounds, more or less, depending upon the baling equipment available. Neither the size of the bale nor its density of compression is critical for success of the process. The bales of waste are made for the convenience of storage and transport. The waste (baled or not) is transported to a processing site on compact well drained soil where it is shredded and made into a free standing pile at least 10 feet wide and 8 feet high, but preferably 75 feet wide and 30 feet high using a belt conveyor to lift the loose waste to form a cone shaped pile.

While the pile is being built it is moistened with water preferably containing iron salts such as ferric sulfate, ferric chloride or any of the water soluble forms of iron and made slightly acidic. The amount of water used is preferably from about two and one-half to three times the dry weight of the waste. The amount of iron (e.g. as ferric sulfate) is preferably at least 250 parts per million and need not be more than 1000 parts per million based upon the dry weight of the waste.

The interior of the large piles will begin to heat and progress from the interior outward to the surface, decreasing as it approaches the surface. The distribution of heat in the pile and its duration at temperatures above 125°–130° F. is essential for providing a useful material. Thermometers are placed in the pile and record the temperatures in relation to time, after the pile is formed.

BRIEF DESCRIPTION OF THE DRAWINGS

With reference to FIG. 1, preferably the thermometers are placed at the outer (i.e. 10 to 12 inches from the surface) intermediate (i.e. 24 to 30 inches from the surface) and central areas of the gin pile.

FIG. 2 illustrates graphically the daily temperatures of fermenting gin waste at various positions within a pile of the preferred size and shape. A temperature of at least 125°–130° F. must be maintained for several hours, or else contained large pieces of material will not be pasteurized and weed seeds and pests may not be destroyed. The outer fringe of the pile, 10 to 12 inches deep, never reaches 125° F. and in frosty weather the outer 12 to 18 inches may never reach temperatures and times required of pasteurization.

Figure 1:
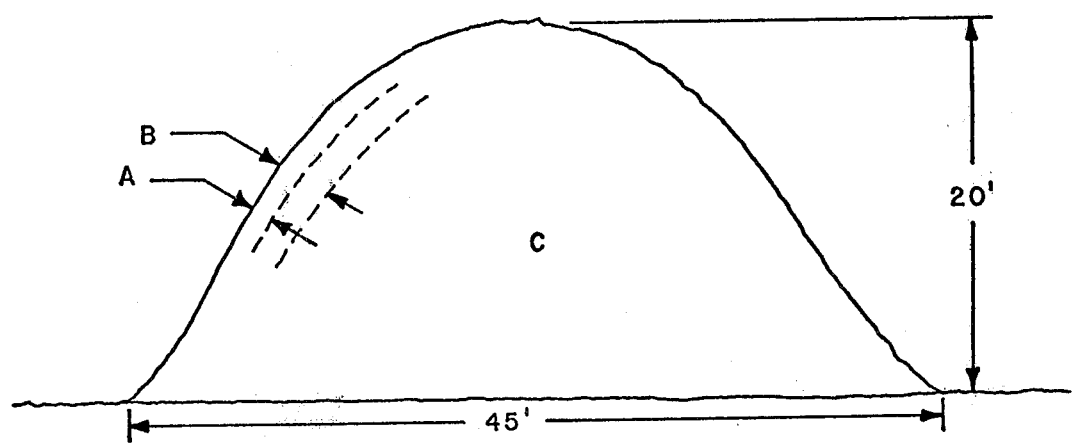
FIG. 1 is a diagram of a pile of gin waste showing shape, preferable size and position of thermometers so that proper fermentation may be controlled.
Figure 2:
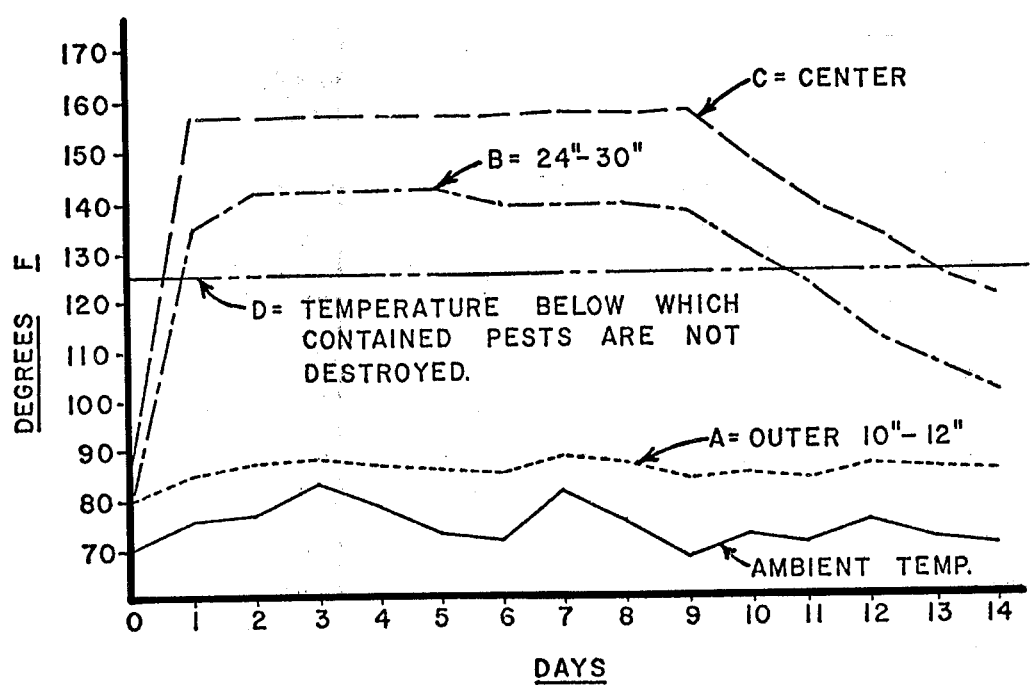
FIG. 2 is a graph of temperatures normally found in a pile of gin waste at depths of: (A) 10″–12″ below surface; (B) 24″–30″ below surface, and (C) center of pile starting at time pile is built and at daily intervals thereafter.

Unless some provision is made for heating the outer layer of the pile it will not be freed of its contained pests and is, therefore, a worthless product which only recontaminates the entire pile.

The present process provides for heating the entire mass by systematically removing the outer portion of the pile, at the base, for example by means of a tractor front end loader, placing the material on a belt conveyor and rebuilding the pile. As the front end loader moves around the pile and removes the material from around the base the outside upper portion of the pile falls. The end result in effect is to turn the pile "outside-in."

The first turning of the pile should be made if the temperatures of the inside center should exceed 170°–180° F. to prevent burn damage. Normally the first turning is made after peak temperatures of 150°–160° F. subside to 130°–140° F. Additional turnings are made after peak temperatures subside until the peak temperature fails to reach 115° to 120° F.

By means of the above process, and with the addition of iron salts, a nitrogen-rich humus is produced with unexpected properties and uses.

The fermented gin waste produced according to the present invention is particularly suitable as a growing medium for plants.

To demonstrate the presence of growth promoting factors composted gin waste was collected, made by the natural process described by Willis and Alberson et al noted above, from Louisiana, Arkansas and Mississippi and subjected the material to tests as follows:

The material was placed in plastic pots in the greenhouse in the early spring. Seeds of cotton and soybeans were planted in the waste and progress of their growth was recorded for a period of 5 weeks. The plants were watered with ion free (mineral free) water.

During the course of the test some of the cotton plants grew luxuriantly, some died, and while the soybeans started to grow they later became yellowish in color and began to die. A chemical analysis of the compost was made with an average of the results shown in Table 1. The results indicated a shortage of iron in the finished compost made by the natural process. A pathological analyses of the affected plants revealed the presence of the plant parasitic fungus *Rhizoctonia solani* which is uniformly present in cotton fields in the Mississippi Delta, (Pinckard, J. A. 1964. *Pellicularia filamentosa* (*Rhizoctonia Solani*), a common saprophyte on mature cotton stems in Louisiana. The fungus is parasitic on seedlings in the spring of the year. Later it becomes saprophytic on mature stems in which it over-winters in the soil, emerging and becoming parasitic again the following spring. The bits and pieces of stems in the waste harbor the fungus unless the temperature of fermentation exceeds 125°–130° F. for several hours and unless all of the waste in the pile receives the heat treatment.

Table 1.

| Chemical composition of a composit of 3 composts of cotton gin waste. Baton Rouge, La. 1972. | |
|---|---|
| pH | 6.8 |
| Nitrogen | 400.0 ppm |
| Phosphorus | 129.0 ppm |
| Potassium | 4150.0 ppm |
| Calcium | 3300.0 ppm |
| Magnesium | 986.0 ppm |
| Boron | 20.0 ppm |
| Copper | 0.3 ppm |
| Iron | 8.0 ppm |
| Zinc | 5.8 ppm |
| Sulfur | 400.0 ppm |
| Conductivity | 430.0 Mhos |
| Moisture holding capacity | 300% |
| Arsenic (Louisiana)* | 0.73 ppm |
| Arsenic (Georgia)* | 0.17 ppm |

*(Normal soils contain 0.3 to 40.0 ppm)

Another test was set up to determine if iron or any of the common minor elements, molybdenum, manganese or copper, was responsible for the failure of the soybean plants to grow normally.

The following rates and sources of the minor elements were added to a similar group of plastic pots, containing 1000 grams each of composted cotton gin waste, then planted with soybean seed:

Molybdenum as ammonium molybdate at:0.25 lbs./A
Manganese as manganese sulfate at:20.00 lbs./A
Copper as cupric sulfate at:5.00 lbs./A
Iron as ferric sulfate at:500.00 lbs./A
Untreated gin waste control:None After 5 weeks of growth in the greenhouse in the early spring, the following growth responses were recorded. The results are set forth in Table 2 below.

Table 2.

| Dry weights and height of harvested tops of soybeans growing in gin waste compost amended with various minor elements listed above. | | |
|---|---|---|
| | Dry wt. in grams | Height of tops in cm. |
| Molybdenum | 0.94 | 23.33 |
| Manganese | 1.14 | 24.33 |
| Copper | 1.71 | 23.00 |
| Iron | 3.55 | 29.66 |
| Untreated gin waste compost control | 1.34 | 23.99 |

Another series of tests, as above, were carried out, but with the addition of ammonium nitrate at an equivalent rate of 500 pounds per acre to each of the pots containing the above minor elements. The results are set forth in Table 3.

Table 3.

| Effect of 500 lbs. per acre of ammonium nitrate, with stated minor elements, on growth of soybean plants in composted cotton gin waste humus. | | |
|---|---|---|
| | Dry wt. in grams | Height of tops in cm. |
| Molybdenum plus nitrogen | 2.59 | 25.00 |
| Manganese plus nitrogen | 2.74 | 25.32 |
| Copper plus nitrogen | 2.48 | 28.33 |
| Iron plus nitrogen | 4.94 | 35.33 |
| Nitrogen alone | 2.46 | 27.66 |

A substantial increase in growth of the test plants both with and without the nitrogen supplement occurred when iron was added as an amendment to the composted cotton gin waste. The soybean test plants in the control pots slowly died after several more weeks.

Obviously, iron is an essential but missing plant food element in the humus formed by composting cotton gin waste regardless of how it may be composted.

Because most field soils contain some iron, especially the red soils of the southern and southeastern part of the country, iron deficiency symptoms may not always be evident. In artificial soils used in certain horticultural practices iron must be added for the normal growth of plants. Obviously, the soil tests made by Willis for testing the fertilizer value of composted gin waste contained sufficient iron for the normal growth of Sudan grass.

Following the discovery of iron deficiency in gin waste and its correction by adding iron salts to the water used in the process of making the compost, or humus, additional tests were made on its value for the growth of plants and the results are set forth in Table 4 below.

Table 4.

| Growth of cotton seedlings after 30 days on thermophyllically fermented cotton gin tailings compared with growth on river loam soil previously fertilized with commercial fertilizer (8-8-8) at the rate of 100 lbs. per acre. | | | | | |
|---|---|---|---|---|---|
| Fermented gin tailings | | | River loam soil | | |
| Replicate No. | Number of seedlings harvested | Seedling Weight (grams) | Replicate No. | Number of seedlings harvested | Seedling Weight (grams) |
| 1 | 32 | 506 | 1 | 36 | 98 |
| 2 | 42 | 483 | 2 | 43 | 101 |
| 3 | 33 | 414 | 3 | 38 | 95 |
| 4 | 27 | 320 | 4 | 37 | 78 |

Table 4.-continued

Growth of cotton seedlings after 30 days on thermo-
phyllically fermented cotton gin tailings compared
with growth on river loam soil previously fertilized
with commercial fertilizer (8-8-8) at the rate of
100 lbs. per acre.

| Fermented gin tailings | | | River loam soil | | |
|---|---|---|---|---|---|
| Replicate No. | Number of seedlings harvested | Seedling Weight (grams) | Replicate No. | Number of seedlings harvested | Seedling Weight (grams) |
| Totals | 134 | 1723.0 | | 154 | 372.0 |
| Ave. | | 12.4 | | | 2.7 |
| Gain = 4.59 times | | | | | |

The cause of the increased rate and total growth of plants in the humus made by the present process is not known. Organic gardeners and farmers have reported improved growth of plants when using various composts in the growing media. Most of these reports have been discredited by the scientific community (Allison, F. E. 1973. Soil Organic Matter and its Role in Crop Production. Elsevier Scientific Publishing Co., N.Y. 637 pps. Chapt. 28, p. 558–582). Nevertheless, humus made from gin waste according to the present process does improve plant growth over and above that expected. The reason is unknown, however, iron is an important element in the growth requirements of plants, microorganisms and animals including man. Ferric iron, however, is quite insoluble at neutral pH. Aerobic and facultative microbial cells must have the ability to synthesize phenolates or hydroxamates to solubilize and assimilate the metal. Compounds with these functions are known as sideriophores. Some actinomycetes (the dominate family of microorganisms in the fermentation of gin waste at high temperatures) produce iron-chelating antibiotics, which are called sideromycins and contain the structure necessary for siderophore function.

Results of the above tests demonstrate that gin waste humus made by the natural processes described by published reports is deficient in iron and may carry *Rhizoctonia solani* and other plant disease causing microorganisms. It follows, of course, that other plant pests may also pass unharmed through the natural composting process.

RESPONSE TO DISEASE AND STIMULATION OF PLANT GROWTH

In a typical experiment on the ability of the thermophyllically fermented cotton gin waste of the invention to suppress a plant disease causing agent the following experiment was set up. Four seed flats were used: two with the thermophyllically fermented gin waste and two with sphagnum peat. Fifteen grams of *Rhizoctonia solani* infested millet seed were mixed in with one flat of sphagnum peat and one of fermented gin waste. After keeping the flats moist for five days all four flats were then plated with 100 seed of pole beans (variety Dade). The results of the experiment 14 days after planting are presented in Table 5 above.

There is illustrated in the above representative test of the ability of thermophyllically fermented gin tailings to reduce the common soil borne *Rhizoctonia solani* fungus. Similar tests using cotton seedlings gave similar results. In the tests using cotton seedlings the disease was driven out of the inoculated fermented gin waste after three replantings, illustrating the antibiotic activity of the residual microbial population. However, the disease increased in severity in the sphagnum peat medium because there were no anti-fungal agents present to inhibit the test fungus *Rhizoctonia solani*.

Additional experiments were conducted in which diseased cotton seed were planted in the thermophyllically fermented gin waste along with disease free seed. The *Rhizoctonia solani* infested seed caused diseased seedlings but there was no spread of the soil borne plant pathogenic fungus *Rhizoctonia solani* to closely adjacent seedlings.

These tests were repeated many times during the course of work identifying percentage of diseased cotton seed in commercial seed samples in commercial seed quality tests.

The thermophyllically fermented cotton gin waste of the invention provides a method for controlling the rate of damping-off of plant seedlings caused by plant parasitic fungi by planting the seedlings in a horticultural medium containing the fermented cotton gin waste in an amount effective to reduce the growth of damping-off fungi. Tests were conducted wherein cotton seedlings were grown in a commercially available potting soil alone and with varying mixtures (i.e. 12.5, 25 and 100 percent) cotton gin waste processed according to the present invention. Each pot was infested with equal amounts of *Rhizoctonia solani*. After 14 days the seedlings in the commercial potting soil alone were about half the size or smaller than those containing the humus gin waste, thus illustrating the suppression of *Rhizoctonia solani*. The presence of iron salts and water in the gin waste plus the high temperatures of fermentation in an aerobic habitat reduces the waste to a humus which does not support the growth or survival of plant parasitic microorganisms.

The cause of the observed suppression is thought to be the presence of antibiotic compounds in the material and/or the vigorous growth ability of competing microorganisms present in the material.

Tests were set up to explore the causes of the suppressive action. A "tea" was made of the waste and sterilized in an autoclave at 240° F. and 10 pounds steam Table 5

A comparison of growth and disease development of pole
bean seedlings on *Rhizoctonia solani* inoculated and
uninoculated sphagnum peat and thermophyllically
fermented gin tailings 14 days after planting.

| Flat No. | Seedling Emergence % | No. Healthy | No. Dead | Total Weight (Grams) |
|---|---|---|---|---|
| 1. Gin waste infested with *Rhizoctonia solani* | 65 | 56 | 9 | 198.0 |
| 2. Sphagnum peat infested with *Rhizoctonia solani* | 31 | 16 | 15 | 71.5 |
| 3. Gin waste not infested | 72 | 71 | 1 | 270.0 |
| 4. Sphagnum peat uninfested | 30 | 24 | 6 | 84.5 | pressure on three consecutive days. A few drops of the sterilized liquid was placed on a plate of bacteriologically sterile nutrient agar. Alongside these drops was then seeded a pure culture of *Rhizoctonia solani*. The fungus refused to grow near the drops of sterilized gin waste liquid, but grew well in the opposite direction, indicating that antibiotic substances were diffusing out into the agar from the liquid.

A similar test was set up in which a small bit of composted gin waste was planted on one side of a nutrient agar plate while on the other side a bit of pure culture of the fungus was also planted. Microorganisms present in the gin waste promptly grew across the plate, in a matter of hours, and engulfed the fungal colony which made no further growth response.

The present invention is useful as a means of controlling pests contained in the gin waste.

Recent environmental regulations now in effect and enforced by the Animal and Plant Health Inspection Service (APHIS) of the U.S. Department of Agriculture prohibits the movement of gin waste, either raw or processed, from the site on which produced if the material contains certain named insect pests (the pink boll worm, for example), noxious weeds (bind weed, Johnson grass and nutsedge), plant disease causing agents and nematodes (soybean cyst and root knot).

By constructing a large free standing pile, e.g., 10 feet wide and 8 feet high, but preferably 30 feet high and 75 feet wide, or larger, so as to minimize the volume of the unheated or partially heated surface in relation to the heated interior volume, according to the present invention one is able to improve the efficiency of decontamination as required by APHIS. Additionally, by using a machine front-end loader, one can rebuild the large pile by systematically removing the surface material from the bottom and sides of the pile, placing it on an elevator so as to deposit it in the interior of the new pile. In this way, the pile can be turned "outside in" so to speak, and be assured that the entire mass would receive sufficient heat for complete decontamination.

Additionally, by inserting thermometers at various depths within the pile and by systematically recording temperatures it now becomes possible to control the fermentation which affects important uses of the humus end product. Unequal distribution of the heat in which pockets of material do not reach at least 125° to 135° F. for several hours will not rid the end product of weed seeds and pests.

The present invention further provides for the removal of pesticidal residues from gin waste. In growing the vast acreages of cotton in the United States the use of pesticidal and harvest aid chemicals on the crop results in important residues remaining in the gin waste. These residues can become a hazard to users of the waste if not removed.

One would expect such chemicals as Toxaphene-DDT, Dieldrin, Aldrin and the arsenic preparations to endure the fermentation process and contaminate the finished humus product rendering it useless as an horticultural growing medium for the usual house plants and home gardens. Surprisingly, none of these poisons survive the long period (several weeks) of oxidative, thermophyllic fermentation.

One of the most sensitive of all tests for the presence of these and similar poisons is to submit samples of the finished product to the fungus gnat of the genus Sciara, family Mycetophylidae. This small insect feeds on the mycelium of fungi in decaying organic matter, and if insecticidal poisons are present the mortality of the flies will so indicate. Caged fungus gnats completed their life cycles normally on the humus made by the present process, indicating the finished product to be free of insecticidal poisons. Although chemical analysis shows the presence of arsenic in the finished material, it does not appear to be in soluble form. Humus is a well known "sink" for arsenic.

The composted gin waste of the present invention may thus be used as an amendment to soils and horticultural growing media for plant propagation and stimulation of growth.

A mixture of gin waste humus with red clay, for example, using as little as one-eighth by volume of the humus and seven-eighths by volume of the red clay has been found to stimulate the growth of Bahia grass, cotton seedlings and other plants.

Humus made from cotton gin waste by the present process is almost neutral in reaction and will be in the pH range of 6.5 to 7.5 or more nearly pH 6.8 to 7.2, which is an excellent range for many kinds of plants such as cabbage, beets and beans. But for many plants including flowers, such as daisies, and especially azaleas and rhododendrons, the growing medium should preferably be of an acid reaction. By mixing gin waste humus with an acid peat having a pH of about 4.5 in ratios of about 1 to 1 or 1 to 3 by volume, a better product for acid loving plants may be made. Mixtures of gin waste humus with perlite, vermiculite, ground wood bark, saw dust, or any of the peat-lite mixes described by Cornell University (Boodley, James W. and Ramond Shelldrake, Jr. 1973. Cornell. Peat-Lite Mixes for Commercial Plant Growing. Cornell Univ. Information Bulletin No. 43, Ithaca, N.Y.) as artificial soils will result in an excellent horticultural growing medium. The above described mixes for horticultural use are clearly different in a number of ways from those conventionally used.

First, gin waste humus made by the present process is not pasteurized as are many of the other horticultural plant growing media. Pasteurization, fumigation, or heat is mandatory for most horticultural growing media to be free of destructive soil borne plant parasitic fungi and other plant disease causing agents.

Secondly, by mixing cotton gin waste humus made according to the present process with the components of artificial soils, or with combinations of materials to make artificial soils, a new formulation results in which as little as 10 percent but preferably 25 or more (i.e. 50%) percent of gin waste humus by volume results in the suppression of the Damping-Off fungus *Rhizoctonia solani* and other similar soil borne plant disease causing agents as determined by tests described above. Additionally, stimulation of plant growth over and above that to be expected by the plant food content of the waste results from its use.

The humus gin waste of the present invention is suitable as a cultural medium for mycorrhizal fungi. Mycorrhizal fungi are a group of soil inhibiting fungi of many species which entwine themselves about the roots of certain plants, the best known of which are forest trees. The plants and the mycorrhizal fungi live in a symbiotic relationship each providing the other with benefits assumed to be derived from food. The fungi have the ability to extract plant foods from the soil making it available to the host plant's roots. The host plant is thought to exude food for the fungus from its roots. Although the mycorrhizal fungi have been known and studied for many years they have not been generally grown in pure culture as have the legume nodule bacteria for commercial use (Marks, G. C. and T. T. Kozlowski. 1973. Ectomycorrhizae Their Ecology and Physiology. Academic Press, New York).

Methods of transferring the mycorrhizal fungi from plants on which they exist to plants on which they are not present requires the transfer of infested roots and soil to the new site where they may or may not find a suitable habitat and attach themselves to the new host plant roots. Commercial use of mycorrhizal fungi could be greatly enhanced if they could be easily grown in pure culture, as are the legume nodule bacteria, and applied as a water mixture to seed, seedlings and more mature plants.

A major disadvantage of transferring soil containing mycorrhizal fungi to new sites is the potential of spreading unwanted plant disease agents.

Experiments with transferring soil containing mycorrhizal fungi to gin waste humus made by the present process were conducted. The fungi in question were gathered in soil taken from around the roots of several forest trees in the mountains of Colorado. The roots and soil samples of several pounds each were composited, mixed with the gin waste humus and allowed to incubate at room temperature for two months before small samples were mixed with a large volume of gin waste humus in which seeds of the lemon (*Citrus limon*) were planted. Frequent microscopic examination of the soil and roots eventually showed the presence of a mycorrhizal fungus belonging to the genus Endogone which is known to improve the growth of citrus (Kleinschmidt, G. D. and J. W. Gerdemann. 1972. Stunting of Citrus Seedlings in Fumigated Nursery Soils Related to the Absence of Endomycorrhizae. Phytopathology 62:1447–1453). The Endogone species, symbionic on the lemon seedling roots, have now been established in the gin waste humus. If kept damp and at normal room temperature the fungi may be recovered and identified at will by growing citrus seedlings in the inoculated gin waste humus. The mycorrhizal fungus of the genus Endogone has now been increased and grown for over a year in gin waste humus made by the present process. Other species of mycorrhizal fungi are also present in the humus.

Of particular note is the use of gin waste humus for correction of young tree decline such as young tree decline of citrus, die-back of camellia and short-life of peach. In view of the fact that cotton gin waste humus made by the present process suppresses the growth of the Damping-Off fungi, and because of its organic plant food content, and the high population of microorganisms present and able to break down organic matter to humus, the ability of the material to correct fruit tree decline as represented by the disease of citrus in Florida known as citrus "Young Tree Decline" was tested. (DuCharme, E. P. 1971. Tree Loss in Relation to Young Tree Decline and Sand Hill Decline of Citrus in Florida. Florida State Horticultural Society 1971:48–52). Cotton gin waste humus, made by the present process, was applied to citrus trees affected with Young Tree Decline. Various rates and methods of application were tested. Trees in a state of decline began showing signs of recovery by the end of the year after application of 100 pounds of the humus material under the canopy and extending outward beyond the outer fringe of leaves. The material was worked into the soil with tractor drawn equipment (e.g. a disc).

Subsequently, the material has been tested in the above described manner and at the rate of 100 pounds of gin waste humus per tree. As a result, trees in a state of decline that have not gone beyond the point of no return have shown regrowth and recovery from Young Tree Decline.

The cause of improved growth of citrus trees affected by decline with gin waste humus is unknown, as is the cause of fruit tree declines in general. Several theories have been proposed to explain the improved growth of decline affected trees treated with gin waste humus. One is the presence of antibiotics; another is the presence of growth promoting substances, both of which are shown to be present in the gin waste humus for the first time and disclosed herein.

The gin waste humus is useful as a selective cultural medium for certain fungi and bacteria used as food and for agronomic purposes. I have found further that the thermophyllically fermented cotton gin waste of the present invention supports the growth of the common mushroom and other species of both fungi and bacteria so that as a microbial culture media it has many uses, particularly as a medium or carrier for anti-fungal microbial agents, plant growth promoting microbial agents such as the Rhizobia, Azotobacter and Mycorrhizae (in both endo and ecto forms).

The cotton gin waste according to the present invention provides an excellent medium for the culture of the common mushroom, a Basidiomycete.

Thus, the thermophyllically fermented cotton gin waste of the present invention is broadly useful as a vehicle for the cultivation of microorganisms beneficial to agriculture. Examples of these beneficial microorganisms include, but are not limited to, such species of fungi as *Agaricus bisporus* and *Morchella esculenta*, the edible mushrooms; the endo- and ecto- Mycorrhizas; and the Rhizobium and Azotobacter groups of bacteria. Cotton gin waste humus as disclosed in this invention may be used either alone or fortified with certain carbon compounds such as the 5 and 6 carbon sugars and the common specific plant food elements or macro- and micro- elements such as the salts of potassium, phosphorus, nitrogen, sulphur, calcium, iron, magnesium and chlorine.

Gin waste humus made by the present process was allowed to air dry on the laboratory bench for several days. It was then ground to a flour-like powder and used to absorb a liquid culture of the legume nodule bacteria *Rhizobium japanicum*. The mixture was stored for eight months in an air tight container, then tested on soybean roots for nodule formation which proved to be positive. From these tests it can be seen that cotton gin waste humus made by this process is a suitable medium for storing Rhizobial cultures. The same technique was applied to growth and storage of Agrobacterium.

The invention in its broader aspects is not limited to the specific details shown and described, but departures may be made from such details within the scope of the accompanying claim without the parting from the principles of the invention.

The invention may furthermore comprise, consist or consist essentially of the hereinbefore recited materials and steps.

What is claimed is:

1. A method for controlling the rate of damping-off of plant seedlings caused by plant parasitic fungi which comprises planting said seedlings in a medium which contains a horticultural medium in an amount effective to reduce the growth of damping-off fungi, said horticultural medium having been produced by the process of aerobically fermenting cotton gin waste to biodegrade the waste at a temperature of at least 125° F. with water in an amount ranging from 1 to 5 times the dry weight of the gin waste, said gin waste being in a pile at least 10 feet wide and 8 feet high to conserve self-generated heat in the interior of the pile, and systematically turning the exterior of the pile to the interior so that all particles of the gin waste are heated to a temperature of from 125° to 180° F. for at least several hours, whereby the gin waste is freed of any soil borne plant diseases, weed seeds, insects or nematodes present therein.

2. A method according to claim 1 wherein the seedlings are sugar beet seedlings.

3. A method according to claim 1 wherein the fermented gin waste is characterized by containing antibiotic agents formed by such process and substantial freedom from insecticidal, herbicidal and plant growth regulants present in the cotton gin waste prior to said fermenting.

4. A method according to claim 1 wherein said water contains at least 250 parts of an inorganic water-soluble iron salt per million parts dry weight of the gin waste.

5. A method according to claim 4 wherein said iron salt is selected from the group consisting of ferric sulfate, ferric chloride and mixtures thereof and is present in an amount ranging from 250 to 1000 parts per million.

6. A method according to claim 1 wherein said horticultural medium has admixed thereto in an amount of from 50 to 90% by weight of a material selected from the group consisting of peat, perlite, vermiculite, sand, wood bark and mixtures thereof.

7. A method according to claim 1 wherein the horticultural medium also contains from about 50 to 90% by weight of clay or sandy soil.

8. A method for improving the rate of tree growth which comprises placing about the locus of a tree a horticultural medium in an amount effective to improve the rate of growth of said tree, said horticultural medium having been produced by the process of aerobically fermenting cotton gin waste to biodegrade the waste at a temperature of at least 125° F. with water in an amount ranging from 1 to 5 times the dry weight of the gin waste, said gin waste being in a pile at least 10 feet wide and 8 feet high to conserve self-generated heat in the interior of the pile, and systematically turning the exterior of the pile to the interior so that all particles of the gin waste are heated to a temperature of from 125° to 180° F. for at least several hours, whereby the gin waste is freed of any soil borne plant diseases, weed seeds, insects or nematodes present therein.

9. A method according to claim 8 wherein from about 75 to 200 pounds of said medium per tree is applied.

10. A method according to claim 9 wherein about 100 pounds of said medium is applied.

11. A method according to claim 8 wherein the fermented gin waste is characterized by containing antibiotic agents formed by such process and substantial freedom from insecticidal, herbicidal and plant growth regulants present in the cotton gin waste prior to said fermenting.

12. A method according to claim 8 wherein said water contains at least 250 parts of an inorganic water-soluble iron salt per million parts dry weight of the gin waste.

13. A method according to claim 12 wherein said iron salt is selected from the group consisting of ferric sulfate, ferric chloride and mixtures thereof and is present in an amount ranging from 250 to 1000 parts per million.

14. A method according to claim 8 wherein said horticultural medium has admixed thereto in an amount of from 50 to 90% by weight of a material selected from the group consisting of peat, perlite, vermiculite, sand, wood bark and mixtures thereof.

15. A method according to claim 8 wherein the horticultural medium also contains from about 50 to 90% by weight of clay or sandy soil.

* * * * *